United States Patent [19]

Ghyczy et al.

[11] 4,309,420

[45] Jan. 5, 1982

[54] STABLE INJECTABLE SOLUTIONS OF INDOLEACETIC ACID DERIVATIVES

[75] Inventors: Miklos Ghyczy; Götz Ritzmann; Adorjan Erdös; Eugen Etschenberg, all of Cologne, Fed. Rep. of Germany

[73] Assignee: A. Nattermann & Cie. GmbH, Cologne, Fed. Rep. of Germany

[21] Appl. No.: 139,117

[22] Filed: Apr. 10, 1980

[30] Foreign Application Priority Data

Nov. 4, 1979 [DE] Fed. Rep. of Germany ....... 2914789

[51] Int. Cl.$^3$ .................... A61K 31/40; A61K 31/685
[52] U.S. Cl. .................................... 424/199; 424/274
[58] Field of Search .............................. 424/199, 274

[56] References Cited

U.S. PATENT DOCUMENTS 3,169,094 2/1965 Wretlind .......................... 424/199

*Primary Examiner*—Stanley J. Friedman
*Attorney, Agent, or Firm*—Burns, Doane, Swecker & Mathis

[57] ABSTRACT

Stable solutions of anti-inflammatory indoleacetic acid derivatives and indanacetic acid derivatives comprise the said derivative and a phospholipid. Such solutions can be administered by injection and have a long-lasting therapeutic effect.

14 Claims, No Drawings

STABLE INJECTABLE SOLUTIONS OF INDOLEACETIC ACID DERIVATIVES

DESCRIPTION

The inflammation-inhibiting action of indoleacetic and indanacetic acid derivatives, such as, for example, Indometacin, has been known for a long time. These active substances are therefore preferentially and successfully employed for the treatment of inflammatory illnesses, such as rheumatism. It is a disadvantage of this therapy that these compounds, when administered orally, often are not well tolerated and cause, for example, ulceration and inflammation of the gastro-intestinal tract. For this reason the therapy of inflammatory illnesses must, not infrequently, be interrupted when such intolerance occurs.

It is accordingly desirable to have available a form for administration of these compounds which circumvents the gastro-intestinal tract or does not expose it to locally severe conditions. An injectable form for administration should be suitable for this purpose, particularly since it would also offer other advantages, such as rapid onset of action, the possibility of applying it locally, and better bioavailability. Because of the low solubility of the active substances, however, the preparation of a parenterally administrable form for administration of the indoleacetic acid and indanacetic acid derivatives has not hitherto been possible.

There has been no lack of attempts to prepare a parenterally administrable form of the indoleacetic acids and indanacetic acids. Even though the free acids have extremely low solubility in water, and a therapeutically active concentration in water cannot be achieved with the free acids, it is possible to prepare aqueous solutions of the desired concentration by dissolving the alkali metal salts. However, in such solutions the substances undergo cleavage after as little as one hour, and the activity of the solutions disappears.

U.S. Pat. No. 4,093,733 therefore proposes to prepare a suspension of Indometacin as a possible galenical form for parenteral administration. It is true that an adequate concentration can be achieved in this way; however, to achieve a reasonably homogeneous suspension, several auxiliaries must be added simultaneously, so that the suspension can under no circumstances be administered intravenously.

German Offenlegungsschrift No. 1,923,574 discloses an attempt to overcome the disadvantages of the low solubility of the indolylacetic acids by preparing the dry sodium salts. Here, the aqueous solutions of the alkali metal salts are freed from water, for example by lyophilisation, immediately after they have been formed. This gives a powder which can easily be redissolved in water. Since, however, the desired removal of the water cannot be taken to completion, the powders thus obtained are still not reliably stable, since the active substance is gradually cleaved hydrolytically by remaining traces of water.

To achieve stability of the alkali metal salt powder, German Offenlegungsschrift No. 1,923,574 has proposed obtaining a dry substance formulation through the addition of strongly basic amines and of a 5-fold to 10-fold amount by weight of a filler. The basic pH value of the solutions prepared from this formulation, makes the use of the latter of dubious safety. In German patent specification No. 1,767,212, at least 50% by volume of a non-aqueous organic solvent is added, together with organic amines. The concentration of 10 mg/ml of 3-indolylacetic acid derivative which this achieves is insufficient for therapeutic success, and furthermore the use of large amounts of organic solvents for an injection solution is not entirely safe.

It is known that some substances which are normally sparingly soluble in water can be made more soluble by means of detergents. Thus, for example, in German Offenlegungsschrift No. 2,730,570 a micelle-forming agent (gallic acids) and a phospholipid are employed as auxiliaries. As is clear from the Examples, the addition of gallic acids is absolutely essential to achieve solubilisation. German Offenlegungsschrift No. 2,315,609 also describes a process for dissolving Indometacin in water. Here again it is necessary to use gallic acids, such as, for example, dehydrocholic acid. The latter is employed in a 110-fold amount by weight, relative to Indometacin. Furthermore, only 0.18 percent by weight of Indometacin can in this way be dissolved in water. To administer a customary therapeutic dose of 50 mg of Indometacin it would thus be necessary to inject 28 ml of this solution. If other, nonionic, surfactants are used, the concentration achieved is again not substantially different (H. Krasowska, Pharm. Ind. 40,1381-4 (1978)). However, the gallic acids employed in both processes themselves exhibit undesirable pharmacological actions (such as, for example, an increase in transaminases) and are therefore to be regarded as unsafe for parenteral use.

Attempts have also been made to administer sparingly water-soluble substances in the form of liposomes, cf. German Offenlegungsschriften Nos. 2,818,655, 2,601,207, 2,712,030 and 2,712,031. Here, the active substance is encapsulated in vesicles of phosphatidylcholine and auxiliaries. Because of the nature of the method of preparation, the yield of enclosed substance is less than 60%. The non-enclosed active substance must be separated in an involved manner by physical methods. In preparing the liposomes, chloroform must usually be used as the solvent. Since this very toxic solvent forms non-volatile complexes with phosphatidylcholine (M. Okazaki, Chem. Phys. Lipids 1976, 17 (1), 28.7), it is not possible to remove enclosed chloroform from the liposomes.

In addition to the unsafe solvents, cholesterol and stearylamine or phosphatic acid must be employed in addition to phosphatidylcholine in preparing the liposomes. Because of the known toxicity of stearylamine and phosphatic acid the parenteral administration of medicaments which contain these substances is not safe.

It has now been found, surprisingly, that indoleacetic acid derivatives and indanacetic acid derivatives, such as Indometacin (1-(p-chlorobenzoyl)-5-methoxy-2-methyl)-indole-3-acetic acid), Acemetacin (1-(p-chlorobenzoyl)-5-methoxy-2-methyl)-indole-3-acetic acid glycolic acid ester), Cinmetacin (1-cinnamoyl-5-methoxy-2-methyl-indole-3-acetic acid) and Sulindac (5-fluoro-2-methyl-1-(p-methylsulphinyl)-benzylidene-indene-3-acetic acid) can be converted into stable aqueous solutions with the aid of phospholipids, without adding further auxiliaries. In this process, novel water-soluble complexes are apparently formed.

The solutions are exceptionally suitable for parenteral administration (for example intramuscular or intravenous administration) of the indoleacetic acid derivatives and indanacetic acid derivatives described above and exhibit a long-lasting inflammation-inhibiting action.

They are both excellently tolerated and also have a long-lasting action. In animal experiments, for example, it has been found that even 11 hours after a single parenteral administration the action is 3-6 times greater than in the case of a single oral administration of the same dosage.

The solution can be prepared by bringing the individual constituents together and homogenising them by stirring in accordance with customary methods. It is not necessary to dissolve one of the constituents beforehand.

A preferred process consists of suspending the indoleacetic acid derivative or indanacetic acid derivative in 20 to 250 parts of water, adding the phospholipid, and stirring vigorously until the mixture is homogeneous. The molar ratio of active substance to phospholipids in this process is from 1:0.5 to 1:10 ratios from 1:0.5 to 1:0.7, and from 1:5 to 1:7, being particularly preferred.

Before or after the preparation of the homogeneous solutions, additives which render the solutions isotonic, such as sodium chloride, glucose or the like, can be added. It is also advantageous to add a base, such as, for example, sodium hydroxide solution or a buffer, in order to give a pH value which is close to the physiological pH value. The solutions thus prepared can be sterilised, and packed in ampoules, in the usual manner, or can be lyophilised, the resulting dry substance being converted into the desired solution when required. Using the process according to the invention, concentrations of 1-80 mg of active substance per ml of solution can be achieved.

Since some of the phospholipids used are sensitive to oxidation and to light, it is advantageous to carry out the process with exclusion of oxygen, under a protective gas atmosphere. Exclusion of light is also advantageous.

Suitable phospholipids are natural and synthetic phospholipids. Suitable natural phospholipids (of vegetable or animal origin) are, in particular, phosphatidylcholine, phosphatidylethanolamine, phosphatidylinositol, phosphatidylserine, spingomyelin, cephalin, lysolecithin, phosphatidylglycol, cardiolipin, plasmalogens, which can be obtained, for example, from soya beans or from egg, and mixtures of these phospholipids, for example the commercially available phosphatidylcholines or phosphatidylcholine mixtures, such as Phospholipon ® 100 (95% pure natural phosphatidylcholine from soya beans)

Phospholipon ® 100 H (98% pure fully hydrogenated phosphatidylcholine from soya beans)

Phospholipon ® 80 (phospholipids from soya beans, containing 75% of phosphatidylcholine and 12% of phosphatidylethanolamine)

Phospholipon ® 55 (alcohol-soluble phospholipids from soya beans, containing 55% of phosphatidylcholine).

Examples of suitable synthetic phosphatides are ditetradecanoylphosphatidylcholine, dihexadecanoylphosphatidylcholine, dioleylphosphatidylcholine and dilinolylphosphatidylcholine, and especially dipalmitoylphosphatidylcholine.

The phospholipids have the advantage, over the substances described for this purpose in the literature, that they are substances which occur in the body, are easily degraded in the body, show no side-effects on long-term treatment (see Weihrauch, U.S. Dept. of Agriculture, quoted in the National Enquirer of 6.6.1978, Page 33) and themselves do not show any analgesic or anti-inflammatory action.

The solutions thus prepared are mechanically and chemically very stable.

The chemical stability was tested by customary methods, for example by thin layer chromatography. No decomposition was observable on storage at room temperature. The solutions prepared in accordance with the processes described above can also be lyophilised by methods known per se (see, in this context, German Patent Application P 28 5633.9). Lyophilisation gives dry substances which can very easily be redissolved in water. The shelf life is also very good. Thus, no decomposition was detectable even at 45° C. storage temperature.

The anti-inflammatory activity was determined by the Hillebrecht rat paw oedema test (J. Hillebrecht, Arzneimittelforschung 4, 607 (1965)). In this test, an oedema was produced in one rear paw of rats weighing 200-250 g each by sub-plantar administration of carrageenin (0.5% in 0.9% NaCl solution), using 0.1 ml of solution per paw. After administering the test substance, in a volume of not more than 10 ml/kg of body weight, the volume of the paw is determined by a displacement method. To test the long-term action, the substance was administered 4, 6 and 8 hours before the administration of the carrageenin. The final value is found three hours after administration. For each dose, the experiment is carried out with 10 test animals and 10 control animals, all of the same sex, and is repeated with the same number of animals of the other sex. For evaluation, the percentage inhibition of the oedema compared to the control group is recorded.

In the accompanying drawing, the result of the oral administration of Indometacin is plotted in comparison with the intramuscular administration of Indometacin plus Phospholipon ® 100. The drawing shows the much longer lasting effect of solutions of the present invention administered by injection compared with Indometacin itself administered orally.

The following Examples illustrate the invention.

EXAMPLE 1

175 mg of Indometacin and 2.35 g of Phospholipon 100 in 30 ml of water are stirred under a homogeneou solution is formed. This is made up to 50 ml with wa ter and is again stirred until a clear, yellow solution i obtained.

EXAMPLE 2

180 mg of Acematacin are stirred with 2.077 g of Phospholipon 100 in 50 ml of isotonic sodium chloride solution, which is brought to pH 6.8 with sodium hydroxide solution, until a homogeneous solution results. This solution is lyophilised in portions of 4 ml. A storage-stable dry substance is obtained. If 1 ml of water is added, a solution containing 14.4 mg of Acemetacin/ml is quickly obtained.

EXAMPLE 3

800 mg of Indometacin and 170 mg of analytical grade NaCl are introduced into 15 ml of water and brought to pH 6.8-7.0 with about 2.1 ml of 1 N NaOH. 1.25 g of Phospholipon 100 are added and the mixture is stirred at 40° C. until all the Phospholipon 100 has dissolved. It is then made up to 20 ml with water and the mixture is treated with ultrasonics until a homogeneous, yellow solution results.

EXAMPLE 4

The procedure described in Example 3 is followed, but 1.25 g of Phospholipon 100 H are employed instead of Phospholipon 100. After the treatment with ultrasonics, a slightly opalescent solution is obtained.

EXAMPLE 5

The procedure described in Example 3 is followed and the resulting homogeneous solution is lyophilised. A stable, slightly yellow dry powder is obtained, which gives a clear solution within 30 seconds if the amount of water which has been abstracted is added back.

EXAMPLE 6

The procedure described in Example 1 is followed, but in addition 650 mg of anhydrous D-glucose are introduced into the solution. A clear, yellow solution is obtained.

EXAMPLE 7

The procedure described in Example 4 is followed, but 1.1 g of dipalmitoylphosphatidylcholine are used instead of Phospholipon 100 H.

EXAMPLE 8

The procedure described in Example 3 is followed, but 1.25 g of Cinmetacin are employed instead of Indometacin.

EXAMPLE 9

The procedure described in Example 3 is followed, but Phospholipon 80 is employed instead of Phospholipon 100.

We claim:

1. A method of treating an inflammatory illness which comprises administering to a subject suffering therefrom an effective amount of a solution comprising a water-soluble complex of a phospholipid and an inflammation-inhibiting indoleacetic acid derivative selected from the group consisting of 1-(p-chlorobenzoyl)-5-methoxy-2-methyl-indole-3-acetic acid, 1-(p-chlorobenzoyl)-5-methoxy-2-methyl-indole-3-acetic acid glycolic acid ester, and 1-cinnamoyl-5-methoxy-2-methyl-indole-3-acetic acid, the molar ratio of said derivative to said phospholipid ranging from about 1:0.5 to 1:10.

2. A method according to claim 1, in which the phospholipid comprises phosphatidylcholine.

3. A method according to claim 1, in which the solution comprises from 1 to 80 milligrams of said derivative per milliliter of solution.

4. A method according to claim 1, in which said derivative comprises 1-(p-chlorobenzoyl)-5-methoxy-2-methyl-indole-3-acetic acid.

5. A method according to claim 1, in which said derivative comprises 1-(p-chlorobenzoyl)-5-methoxy-2-methyl-indole-3-acetic acid glycolic acid ester.

6. A method according to claim 1, in which the molar ratio of said derivative to said phospholipid ranges from about 1:5 to 1:7.

7. A method according to claim 1, in which said derivative comprises 1-cinnamoyl-5-methoxy-2-methyl-indole-3-acetic acid.

8. An injectable stable solution having an inflammation-inhibiting action, comprising a water-soluble complex of a phospholipid and an inflammation-inhibiting indoleacetic acid derivative selected from the group consisting of 1-(p-chlorobenzoyl)-5-methoxy-2-methyl-indole-3-acetic acid, 1-(p-chlorobenzoyl)-5-methoxy-2-methyl-indole-acetic acid glycolic acid ester and 1-cinnamoyl-5-methoxy-2-methyl-1-indole-3-acetic acid, the molar ratio of said derivative to said phospholipid ranging from about 1:0.5 to 1:10.

9. A solution according to claim 8, in which the phospholipid comprises phosphatidylcholine.

10. A solution according to claim 8 which comprises from 1 to 80 milligrams of said derivative per milliliter of solution.

11. A solution according to claim 8, in which said derivative comprises 1-(p-chlorobenzoyl)-5-methoxy-2-methyl-indole-3-acetic acid.

12. A solution according to claim 8, in which said derivative comprises 1-(p-chlorobenzoyl)-5-methoxy-2-methyl-indole-3-acetic acid glycolic acid ester.

13. A solution according to claim 8, in which said derivative comprises 1-cinnamoyl-5-methoxy-2-methyl-indole-3-acetic acid.

14. A solution according to claim 8, in which the molar ratio of said derivative to said phospholipid ranges from about 1:5 to 1:7.

* * * * *

UNITED STATES PATENT AND TRADEMARK OFFICE
CERTIFICATE OF CORRECTION

PATENT NO. : 4,309,420
DATED : January 5, 1982
INVENTOR(S) : MIKLOS GHYCZY et al It is certified that error appears in the above-identified patent and that said Letters Patent is hereby corrected as shown below:

The Foreign Application Priority Data on the first page of the patent which reads "Nov. 4, 1979 [DE] Federal Republic of Germany.....2914789"

should read instead

--April 11, 1979 [DE] Federal Republic of Germany.....2914789--.

Signed and Sealed this

First Day of May 1984

[SEAL]

Attest:

GERALD J. MOSSINGHOFF

Attesting Officer    Commissioner of Patents and Trademarks